United States Patent
Qi et al.

(10) Patent No.: US 12,024,791 B2
(45) Date of Patent: *Jul. 2, 2024

(54) QUALITY PREDICTION METHOD, PREPARATION METHOD AND SYSTEM OF HIGH RESISTANCE GALLIUM OXIDE BASED ON DEEP LEARNING AND EDGE-DEFINED FILM-FED GROWTH METHOD

(71) Applicant: HANGZHOU FUJIA GALLIUM TECHNOLOGY CO. LTD., Zhejiang (CN)

(72) Inventors: Hongji Qi, Hangzhou (CN); Duanyang Chen, Hangzhou (CN); Qinglin Sai, Hangzhou (CN)

(73) Assignee: HANGZHOU FUJIA GALLIUM TECHNOLOGY CO. LTD., Hangzhou (CN)

( * ) Notice: Subject to any disclaimer, the term of this patent is extended or adjusted under 35 U.S.C. 154(b) by 125 days.

This patent is subject to a terminal disclaimer.

(21) Appl. No.: 17/760,964

(22) PCT Filed: Feb. 8, 2021

(86) PCT No.: PCT/CN2021/076071
§ 371 (c)(1),
(2) Date: Mar. 16, 2022

(87) PCT Pub. No.: WO2022/141765
PCT Pub. Date: Jul. 7, 2022

(65) Prior Publication Data
US 2023/0160098 A1     May 25, 2023

(30) Foreign Application Priority Data
Dec. 31, 2020 (CN) .......................... 202011639219.8

(51) Int. Cl.
C30B 15/34 (2006.01)
C30B 15/20 (2006.01)
(Continued)

(52) U.S. Cl.
CPC .............. C30B 15/34 (2013.01); C30B 15/20 (2013.01); C30B 29/16 (2013.01); G16C 20/70 (2019.02)

(58) Field of Classification Search
CPC ......... C30B 15/34; C30B 15/20; C30B 29/16; G16C 20/10
See application file for complete search history.

(56) References Cited

U.S. PATENT DOCUMENTS 11,489,090 B1 * 11/2022 Atanackovic ..... H01L 21/02433
11,502,223 B1 * 11/2022 Atanackovic ............ H01S 5/32
(Continued)

FOREIGN PATENT DOCUMENTS

CN      105603528 A     5/2016
CN      107541776 A     1/2018
(Continued)

OTHER PUBLICATIONS

International Search Report mailed Oct. 11, 2021, in corresponding to International Application No. PCT/CN2021/076071; 3 pages.
(Continued)

*Primary Examiner* — Robert M Kunemund
(74) *Attorney, Agent, or Firm* — Maier & Maier, PLLC

(57) ABSTRACT

A high resistance gallium oxide quality prediction method based on deep learning and an edge-defined film-fed crystal growth method, a preparation method and a system; the quality prediction method includes the following steps: obtaining preparation data of a high resistance gallium oxide single crystal prepared by the edge-defined film-fed crystal growth method, the preparation data including seed crystal
(Continued)

data, environment data and control data, and the control data including doping element concentration and doping element type; preprocessing the preparation data to obtain preprocessed preparation data; inputting the preprocessing preparation data into a trained neural network model, acquiring the predicted quality data corresponding to the high resistance gallium oxide single crystal through the trained neural network model, the predicted quality data including predicted resistivity.

10 Claims, 4 Drawing Sheets

(51) Int. Cl.
*C30B 29/16* (2006.01)
*G16C 20/70* (2019.01)

(56) References Cited

U.S. PATENT DOCUMENTS

| | | | |
|---|---|---|---|
| 2005/0288812 | A1 | 12/2005 | Cheng et al. |
| 2021/0351321 | A1* | 11/2021 | Atanackovic ..... H01L 21/02414 |

FOREIGN PATENT DOCUMENTS

| | | | |
|---|---|---|---|
| CN | 109338456 | A | 2/2019 |
| CN | 109537055 | A | 3/2019 |
| CN | 110033486 | A | 7/2019 |
| CN | 111028893 | A | 4/2020 |
| CN | 111695287 | A | 9/2020 |
| CN | 111893563 | A | 11/2020 |
| DE | 19824838 | A1 | 12/1999 |
| JP | 200624195 | A | 1/2006 |
| JP | 2006-312571 | A | 11/2006 |
| JP | 2011190127 | A | 9/2011 |
| JP | 2013237591 | A | 11/2013 |
| JP | 201613933 | A | 1/2016 |
| WO | 9963134 | A1 | 12/1999 |
| WO | 2013073497 | A1 | 5/2013 |

OTHER PUBLICATIONS

Su Weifeng; "Crystal Growth Prediction Control Based on Neural Network"; China Excellent Master's Degree Thesis Full-text Database (Information Technology Series); Jun. 15, 2005 (Jun. 15, 2005); Issue 2; Section 1.1 and Chapter 2-4; 45 pages.
Mu Wenxiang; "Growth, Processing and Properties of B—Ga2O3 Single Crystal"; Chinese Doctoral Dissertation Full-text Database (Engineering Science and Technology Series I); Jan. 15, 2019 (Jan. 15, 2019); Issue 12; pp. 1-32; 57 pages.
First Examination Report issued Sep. 8, 2021, in corresponding to Chinese Application No. 202011639219.8; 11 pages (with English Translation).
Extended European Search Report issued on Nov. 8, 2022, in corresponding European Application No. 21870470.8, 15 pages.
Kuramata et al., "Bulk Crystal Growth of Ga2O3", Proceedings of SPIE, 2018, vol. 10533, 6 pages.
Mu et al., "High quality crystal growth and anisotropic physical characterization of B—Ga2O3 single crystals grown by EFG method", Journal of Alloys and Compounds, 2017, vol. 714, pp. 453-458.
Office Action issued on Apr. 12, 2023, in corresponding Japanese Application No. 2022-520490, 4 pages.

* cited by examiner

US 12,024,791 B2

QUALITY PREDICTION METHOD, PREPARATION METHOD AND SYSTEM OF HIGH RESISTANCE GALLIUM OXIDE BASED ON DEEP LEARNING AND EDGE-DEFINED FILM-FED GROWTH METHOD

CROSS-REFERENCE TO RELATED APPLICATIONS

This application is a national application of PCT Patent Application No. PCT/CN2021/076071, filed on Feb. 8, 2021, which claims priority to Chinese Patent Application No. 202011639219.8, filed on Dec. 31, 2020. The content of all of which is incorporate herein by reference.

FIELD

The present application relates to the technical field of a high resistance gallium oxide crystal preparation, in particular to a quality prediction method, a preparation method and a system of high resistance gallium oxide based on a deep learning and an edge-defined film-fed growth (EFG) method.

BACKGROUND $\beta$-$Ga_2O_3$ (high resistance gallium oxide) is a direct-gap semiconductor material having a wide band gap, a width of the band gap is about 4.8~4.9 eV. The $\beta$-$Ga_2O_3$ has a plurality of advantages including a large band gap, a fast drift speed of a saturated electron, a high thermal conductivity, a high breakdown field strength, a stable chemical property and more, having a wide range of application prospects in a field of electric or electronic device having a high temperature, a high-frequency, and a high-power. In addition, it can further be used for an LED chip, a solar-blind ultraviolet detection, various sensor components and camera components, and more.

In the prior art, a bulk preparation of a large-size high resistance gallium oxide crystal mainly adopts an EFG preparation technology. The EFG method is a mature single crystal preparation technology, having a plurality of advantages including a special-shaped crystal growth, a fast growth speed and a low growth cost. The EFG method is a crystal growth method improved on a basis of Czochralski method, requiring a crystal growth device and a growth process exploration relatively more complicated. The EFG method requires a mold to be placed in a crucible, and a crystal growth interface is located on an upper surface of the mold. Under a high temperature, due to an effect of a surface tension, a melt rises to the upper surface of the mold along a capillary in the mold. A height H of the melt raised along the capillary is determined by a formula of $$H = \frac{2\gamma\cos\theta}{\rho gr},$$

wherein $\gamma$ is the surface tension of the melt, $\theta$ is a contact angle between the melt and the capillary, $\rho$ is a density of the melt, g is an acceleration of gravity, and r is a radius of the capillary.

Comparing to the Czochralski method, adopting the EFG method to prepare the high resistance gallium oxide crystal has a plurality of following advantages:

1. Melt convection in the capillary of the mold is weak, and it is difficult for a plurality of impurity ions in the melt to return to the crucible after having raised to a solid-liquid interface from the capillary. A segregation coefficient of the impurity ions in the crystal is generally close to 1, thus an impurity distribution on both upper side and lower side in the crystal is consistent;

2. The solid-liquid interface of the crystal growing locates above the mold, and a shape of the interface can be controlled by a geometry shape of a mold surface. A position of the solid-liquid interface in a temperature field is always unchanged and is not affected by a melt disturbance in the crucible. Thus the solid-liquid interface of the crystal growing in the EFG method is more stable;

3. The EFG method has a faster crystal growth rate, beneficial to reduce energy consumption, being able to grow a special-shaped crystal, and reducing a crystal processing cost and a processing loss.

However, during a process of adopting the EFG method to prepare the high resistance gallium oxide crystal, a change of a plurality of parameters including a temperature field distribution near an opening of the mold, a selection of a seed crystal, a pulling speed of a seed crystal rod, an atmosphere and environment of the crystal growth, as well as a heating power, a cooling power and more, may all generate a relatively great impact on a quality of the high resistance gallium oxide crystal produced. The EFG method for preparing the high resistance gallium oxide crystal in the prior art relies totally on an experience of an operator to set a plurality of parameters, a repeatability thereof is poor, resulting in a stability of a product of the high resistance gallium oxide crystal produced relatively poor.

Therefore, the current technology needs to be improved and developed.

SUMMARY

According to the defects in the prior art described above, the present application aims to provide a quality prediction method, a preparation method and a system of high resistance gallium oxide based on a deep learning and an EFG method, in order to solve a plurality of problems in the prior art that the process of using the EFG method to prepare the high resistance gallium oxide crystal relies totally on the experience of an operator to set the parameters, having a relatively poor repeatability, resulting in a quality and the stability of the product of the high resistance gallium oxide crystal produced relatively poor.

The technical solution of the present application to solve the technical problems is as follows:

a quality prediction method of high resistance gallium oxide based on a deep learning and an EFG method, wherein comprising a plurality of steps:

acquiring a preparation data of preparing a high resistance gallium oxide single crystal by the EFG method, the preparation data comprising a seed crystal data, an environment data and a control data, the control data comprising a doping element concentration and a doping element type;

preprocessing the preparation data to obtain a preprocessed preparation data;

inputting the preprocessed preparation data into a trained neural network model, acquiring a predicted quality data corresponding to the high resistance gallium oxide single crystal through the trained neural network model, the predicted quality data comprising a predicted resistivity.

The quality prediction method of the high resistance gallium oxide based on deep learning and the EFG method, wherein the step of preprocessing the preparation data to obtain the preprocessed preparation data, comprising:

according to the seed crystal data, the environmental data, and the control data, obtaining the preprocessed preparation data, and the preprocessed preparation data is a matrix formed by the seed crystal data, the environmental data, and the control data.

The quality prediction method of the high resistance gallium oxide based on deep learning and the EFG method, wherein the seed crystal data comprising: a half-height width of a seed crystal diffraction peak, a deviation value of the half-height width of the seed crystal diffraction peak, a seed crystal thickness and a seed crystal width;

the environmental data further comprising: a thermal resistance value of an upper thermal insulation cover, a deviation value between the thermal resistance values of the upper thermal insulation cover, a shape factor of a crystal growth channel, a shape factor of a crystal growth observation hole, a thermal resistance value of a lower thermal insulation cover, a deviation value between the thermal resistance values of the lower thermal insulation cover, a relative height between a crucible and a heating coil, a relative height between a heating ring and the heating coil, a width of a mold opening gap, and a thickness of the mold opening gap;

the control data comprising: a heating power, a cooling power, an atmosphere type, a cavity pressure, a gas flow, and a seed crystal rod pulling speed.

The quality prediction method of the high resistance gallium oxide based on deep learning and the EFG method, wherein the step of according to the seed crystal data, the environmental data, and the control data, obtaining the preprocessed preparation data, comprising:

according to the seed crystal data, the environmental data, and the control data, determining a preparation vector; wherein a first element in the preparation vector is one of the half-height width of the seed crystal diffraction peak, the deviation value of the half-height width of the seed crystal diffraction peak, the seed crystal thickness and the seed crystal width; a second element in the preparation vector is one of the thermal resistance value of the upper thermal insulation cover, the deviation value between the thermal resistance values of the upper thermal insulation cover, the shape factor of the crystal growth channel, the shape factor of the crystal growth observation hole, the thermal resistance value of the lower thermal insulation cover, the deviation value between the thermal resistance values of the lower thermal insulation cover, the relative height between the crucible and the heating coil, the relative height between the heating ring and the heating coil, the width of the mold opening gap, the thickness of the mold opening gap, the doping element concentration, and the doping element type, the type of the doping element comprising: Fe, Ca, Zn, Co, Ti, Ni, Mg, Al and Cu; a third element in the preparation vector is one of the heating power, the cooling power, the atmosphere type, the cavity pressure, the gas flow, and the seed rod pulling speed;

determining the preprocessed preparation data, according to the preparation vector.

The quality prediction method of the high resistance gallium oxide based on deep learning and the EFG method, wherein the predicted quality data comprising: a predicted crack data, a predicted miscellaneous crystal data, a predicted half-height width of the diffraction peak, a predicted deviation of the half-height width of the diffraction peak, a predicted shoulder symmetry of the high resistance gallium oxide crystal, a predicted left border extending and retracting degree of the high resistance gallium oxide crystal, a predicted right border extending and retracting degree of the high resistance gallium oxide crystal, a predicted thickness of the high resistance gallium oxide crystal, a deviation of the predicted thickness of the high resistance gallium oxide crystal, a predicted radial deviation of the resistivity, and a predicted axial deviation of the resistivity.

The quality prediction method of the high resistance gallium oxide based on deep learning and the EFG method, wherein the trained neural network model is trained and obtained by using a plurality of following training steps:

acquiring a training data of preparing the high resistance gallium oxide single crystal by the EFG method and a corresponding actual quality data, wherein the training data comprising: a seed crystal training data, an environmental training data, and a control training data;

preprocessing the training data to obtain a preprocessed training data;

inputting the preprocessed training data into a preset neural network model, and obtaining a predicted training generated quality data corresponding to the preprocessed training data through the preset neural network model;

adjusting and correcting a plurality of model parameters of the preset neural network model to obtain a trained neural network model, according to the predicted training generated quality data and the actual quality data.

The quality prediction method of the high resistance gallium oxide based on deep learning and the EFG method, wherein the preset neural network model comprising: a feature extraction module and a fully connected module, the step of inputting the preprocessed training data into the preset neural network model, and obtaining the predicted training generated quality data corresponding to the preprocessed training data through the preset neural network model, comprising:

inputting the preprocessed training data into the feature extraction module, and obtaining a feature vector corresponding to the preprocessed training data through the feature extraction module;

inputting the feature vector into the fully connected module, and obtaining the predicted training generated quality data corresponding to the preprocessed training data through the fully connected module.

A preparation method of the high resistance gallium oxide based on deep learning and the EFG method, wherein the preparation method comprising a plurality of steps:

acquiring a target quality data of a target conductivity gallium oxide single crystal, and the target quality data comprising a target resistivity;

determining a target preparation data corresponding to the target high resistance gallium oxide single crystal, according to the target quality data and the trained neural network model, wherein the target preparation data comprising: a target seed crystal data, a target environment data, and a target control data, the target environment data comprising a target doping element concentration and a target doping element type;

preparing and obtaining the target high resistance gallium oxide single crystal according to the target preparation data, based on the EFG method.

The preparation method of the high resistance gallium oxide based on deep learning and the EFG method, wherein determining the target preparation data corresponding to the target high resistance gallium oxide single crystal, according to the target quality data and the trained neural network model, comprising a plurality of steps:

acquiring a preset preparation data, preprocessing the preset preparation data, and obtaining a preprocessed preset preparation data;

inputting the preprocessed preset preparation data into the trained neural network model, and obtaining a predicted quality data corresponding to the preprocessed preset preparation data through the trained neural network model;

correcting the preset preparation data and obtaining the target preparation data corresponding to the target high resistance gallium oxide single crystal according to the predicted quality data and the target quality data.

A preparation system of the high resistance gallium oxide based on deep learning and the EFG method, wherein comprising a storage and a processor, the storage stores a computer program, when the processor executes the computer program, the steps of the quality prediction method are implemented according to any one embodiment of the present application, or the steps of the preparation method are implemented according to any one embodiment of the present application.

Benefits: the present application provides a quality prediction method and a preparation method of the high resistance gallium oxide based on deep learning and the EFG method, first preprocessing the preparation data of preparing a high resistance gallium oxide single crystal by the EFG method and obtaining a preprocessed preparation data, then inputting the preprocessed training data into a preset neural network model, and obtaining a predicted quality data corresponding to the high resistance gallium oxide single crystal through the trained neural network module. The present application may predict the quality of the high resistance gallium oxide single crystal through the trained neural network model, so it is possible to adjust the preparation data to obtain a required performance of the high resistance gallium oxide single crystal, making the performance of the high resistance gallium oxide single crystal be optimized.

BRIEF DESCRIPTION OF THE DRAWINGS

In order to explain a plurality of embodiments of the present application or a technical solution in the prior art more clearly, a briefly introduction to the drawings that need to be used in the description of the embodiments or the prior art is stated herein. Obviously, the drawings described herein are a plurality of embodiments described in the present application only. For those ordinary skilled in the art, other drawings can be obtained based on the present drawings without any creative work.

DETAILED DESCRIPTION OF THE EMBODIMENTS

The present application provides a preparation method and a system of high resistance gallium oxide based on a deep learning and an EFG method, in order to make the purpose, technical solution and the advantages of the present application clearer and more explicit, further detailed descriptions of the present application are stated herein, referencing to the attached drawings and some embodiments of the present application. It should be understood that the detailed embodiments of the application described here are used to explain the present application only, instead of limiting the present application.

Those skilled in the art can understand that, unless specifically stated, a plurality of singular forms "a", "an", "said" and "the" used herein may also comprise plural forms. It should be further understood that the term "comprising" used in the specification of the present application refers to the presence of the described features, integers, steps, operations, elements and/or components, without excluding the presence or addition of one or more other features, Integers, steps, operations, elements, components, and/or groups thereof. It should be understood that when an element is referred as being "connected" or "coupled" to another element, it can be directly connected or coupled to the other element, or an intervening element may also be present. In addition, "connected" or "coupled" used herein may include wireless connection or wireless coupling. The term "and/or" as used herein includes all or any unit and all combinations of one or more associated listed items.

Those skilled in the art can understand that, unless otherwise defined, all terms (including technical terms and scientific terms) used herein have a same meaning as commonly understood by those of ordinary skills in the art to which the present application belongs to. It should also be understood that terms such as those defined in general dictionaries should be understood as having a meaning consistent with the meaning in the context of the prior art, and unless specifically defined herein, they will not be idealized or overly explain the formal meaning.

Further descriptions of the present application are stated hereafter by describing some embodiments of the present application, together with the attached drawings.

Figure 1:
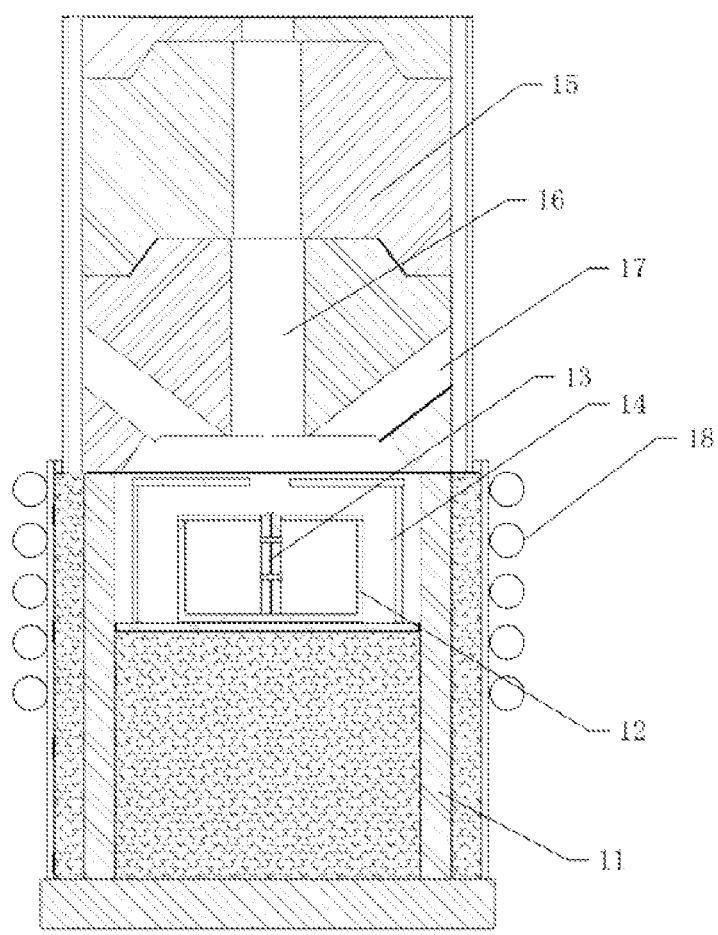
FIG. 1 illustrates a schematic structural diagram of a crystal growth furnace for preparing the high resistance gallium oxide crystal by the EFG method provided by the present application.

The present application provides a crystal growth furnace for growing a high resistance gallium oxide crystal by an EFG (edge-defined film-fed growth) method, shown as FIG. 1, comprising a lower thermal insulation cover 11, the lower thermal insulation cover 11 has a crucible 12 arranged inside, the crucible 12 has a mold 13 forming a capillary siphon effect arranged inside, and a heating ring 14 arranged outside. The lower thermal insulation cover 11 has an upper thermal insulation cover 15 arranged above, and the upper thermal insulation cover 15 has a crystal growth channel 16 arranged inside, and a crystal growth observation hole 17 arranged on a side thereof. The lower thermal insulation cover 11 further has an induction coil 18 arranged outside.

Based on the crystal growth furnace, it is possible to prepare the high resistance gallium oxide crystal. First, the crystal growth furnace for preparing the high resistance gallium oxide crystal shall be installed, comprising a material selection for the upper thermal insulation cover 15, a size of an axial opening of the upper thermal insulation cover 15, a shape and a size of an opening window, a material selection for the lower thermal insulation cover 11, a height position of the crucible 12 relative to the induction coil 18, a relative height between the heating ring 14 and the induction coil 18, and more, all of them will affect a thermal field distribution inside a device thereof, thereby affecting a product performance of the high resistance gallium oxide crystal.

Placing a β-Ga$_2$O$_3$ seed crystal having a specific orientation into a seed crystal fixture before binding and fixing, the orientation of the seed crystal may be [010], [001] direction, and more;

first, a mechanical pump and a diffusion pump are turned on in turn to vacuum an equipment, and when a predetermined vacuum degree is reached, a vacuum equipment is turned off, and a mixed gas is slowly inflated into the equipment according to a volume ratio thereof;

Then, set a heating power, and the crucible is heated by a heating element, making a gallium oxide raw material and a doping element material placed in the crucible completely be molten, before the gallium oxide and the doping element material after being molten are transported to a top of a mold by a capillary siphoning action, before extending on the top until completely covering the top; then, a seed crystal rod is slowly lowered until a seed crystal is 3-5 mm above the top of an iridium mold for preheating, and an inoculation starts in 5-10 minutes; wait until the seed crystal and a melt body are fully welded and connected, before a seeding and necking operation is performed to prevent a plurality of original defects of the seed crystal from extending to an inside of the crystal, ensuring a quality of the crystal. Followed by a shoulder extending is carried out to expand the crystal laterally to an entire mold; further an isodiameter growth is carried out; after a crystal growth is over, it is slowly lowered to a room temperature, before taking out the crystal, and obtaining the high resistance gallium oxide crystal. During a process of preparing the high resistance gallium oxide crystal, a heating power, a cooling power, an atmosphere type, a cavity pressure, a gas flow, and a seed rod pulling speed will all affect the product performance of the high resistance gallium oxide crystal.

Figure 2:
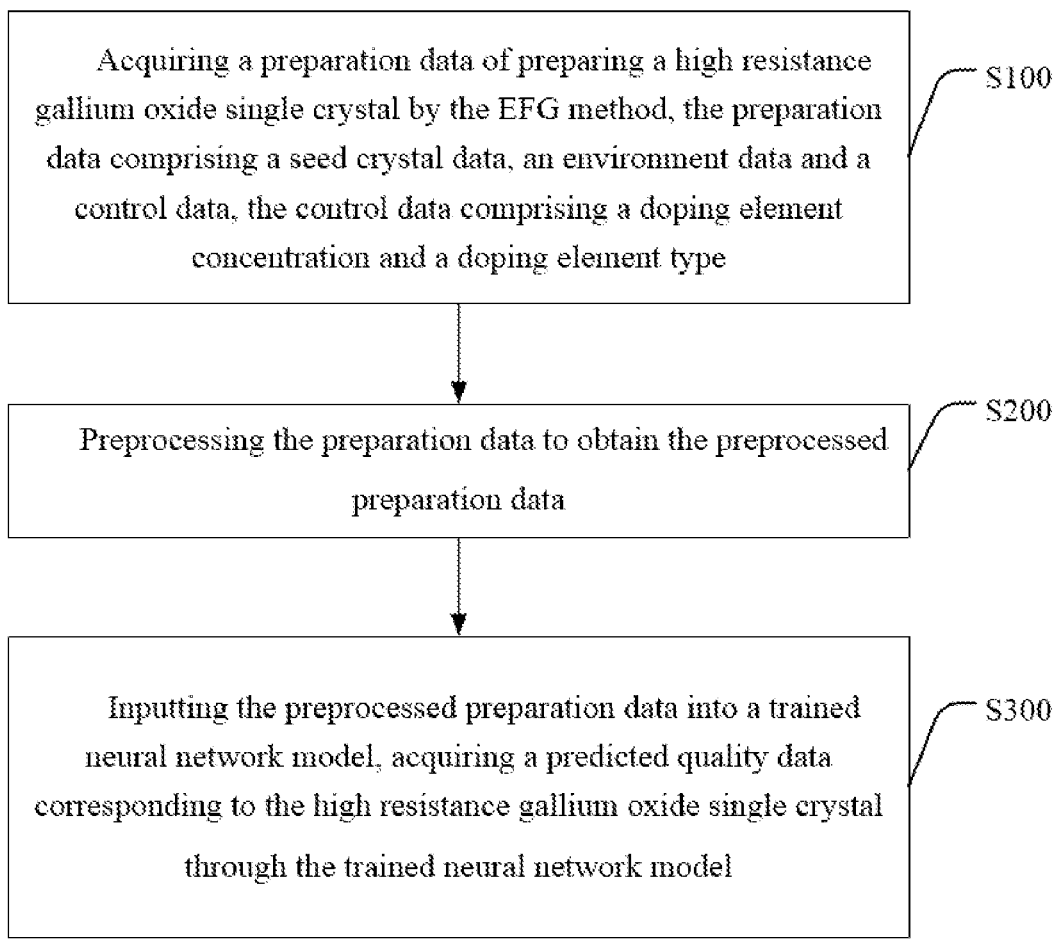
FIG. 2 illustrates a flowchart on a preferred embodiment of the quality prediction method of the high resistance gallium oxide based on deep learning and the EFG method provided by the present application.

Based on that, the present embodiment provides a quality prediction method of the high resistance gallium oxide based on deep learning and the EFG method, shown as FIG. 2, comprising a plurality of following steps:

S100, acquiring a preparation data of preparing a high resistance gallium oxide single crystal by the EFG method, the preparation data comprising a seed crystal data, an environment data and a control data, the control data comprising a doping element concentration and a doping element type.

Specifically, the preparation data refers to a data of the high resistance gallium oxide single crystal prepared by adopting the EFG method, and the preparation data is a data that can be configured according to any requirements. In an embodiment, when it is needed to predict a performance of the high resistance gallium oxide single crystal obtained under a certain preparation data, as long as the preparation data is determined, and preprocessed to obtain the preprocessed preparation data, and the preprocessed preparation data is input into the trained neural network model, it is possible to obtain the predicted quality data through the trained neural network model. That is, there is no experiment required, and as long as the preparation data is determined, it is possible to predict the quality data of the high resistance gallium oxide single crystal through the trained neural network model.

In the present embodiment, the preparation data comprises a seed crystal data, an environment data and a control data, the seed crystal data refers to a plurality of data of the seed crystal used in the process of preparing the high resistance gallium oxide single crystal by the EFG method, the environmental data refers to a plurality of data of an environment that the high resistance gallium oxide single crystal locates during the process of being prepared by the EFG method; the control data refers to a plurality of data controlling a growth of the seed crystal used in the process of preparing the high resistance gallium oxide single crystal by the EFG method. The doping element concentration refers to a concentration of a plurality of doping elements in the high resistance gallium oxide, and the doping element type comprises: Fe, Ca, Zn, Co, Ti, Ni, Mg, Al, Cu, and more.

S200, preprocessing the preparation data to obtain the preprocessed preparation data.

Specifically, after the preparation data is obtained, the preparation data is first preprocessed to obtain the preprocessed preparation data, so that the preprocessed preparation data may be input into the trained neural network model, so as to process the preprocessed preparation data through the trained neural network model.

In an embodiment of the present application, the step of S200, preprocessing the preparation data to obtain the preprocessed preparation data, comprises:

S210, according to the seed crystal data, the environmental data, and the control data, obtaining the preprocessed preparation data, and the preprocessed preparation data is a matrix formed by the seed crystal data, the environmental data, and the control data.

Specifically, after obtaining the preparation data, the preparation data is preprocessed first to obtain the preprocessed preparation data. Since each sub-data (including the seed crystal data, the environmental data, and the control data) in the preparation data are affecting each other, but currently it is not clear for a degree of the sub-data affecting each other. Therefore, it is necessary to preprocess the preparation data, by rearranging and combining each sub-data in the preparation data, to form the preprocessed preparation data.

In another embodiment of the present application, the seed crystal data comprises: a half-height width of a seed crystal diffraction peak, a deviation value of the half-height width of the seed crystal diffraction peak, a seed crystal thickness and a seed crystal width; the environmental data further comprises: a thermal resistance value of the upper thermal insulation cover, a deviation value between the thermal resistance values of the upper thermal insulation cover, a shape factor of the crystal growth channel, a shape factor of the crystal growth observation hole, a thermal resistance value of the lower thermal insulation cover, a deviation value between the thermal resistance values of the lower thermal insulation cover, a relative height between the crucible and the heating coil, a relative height between the heating ring and the heating coil, a width of a mold opening gap, and a thickness of the mold opening gap; the control data comprises: a heating power, a cooling power, an atmosphere type, a cavity pressure, a gas flow, and a seed crystal rod pulling speed.

Specifically, the half-height width of the seed crystal diffraction peak can be tested by an X-ray diffractometer, and the deviation value of the half-height width of the seed crystal diffraction peak comprises a radial deviation value of the half-height width of the seed crystal diffraction peak and an axial deviation value of the half-height width of the seed crystal diffraction peak. A radial direction is a direction on a horizontal plane, and an axial direction is a direction perpendicular to the horizontal plane, or an axis in a vertical direction. The radial deviation value of the half-height width of the seed crystal diffraction peak can be achieved by measuring the half-height width of the seed crystal diffraction peak in a radial direction of the seed crystal, and obtaining a difference between the half-height widths of the seed crystal diffraction peak in the radial direction of the seed crystal, that is obtaining the radial deviation of the half-height width of the seed crystal diffraction peak. The axial deviation value of the half-height width of the seed crystal diffraction peak can be achieved by measuring the half-height width of the seed crystal diffraction peak in an axial direction of the seed crystal, and obtaining a difference between the half-height widths of the seed crystal diffraction peak in the axial direction of the seed crystal, that is obtaining the axial deviation of the half-height width of the seed crystal diffraction peak. The seed crystal thickness and the seed crystal width can be directly measured.

As described above, when adopting the crystal growth furnace shown as FIG. 1 to prepare the high resistance gallium oxide single crystal, both the upper thermal insulation cover 15 and the lower thermal insulation cover 11 provide a stable thermal field for the growth of the high resistance gallium oxide single crystal. The thermal resistance value of the upper thermal insulation cover 15 refers to a temperature difference between an inner side and an outer side of the upper thermal insulation cover when a unit heat passes through the upper thermal insulation cover in a unit period. The larger the thermal resistance of the upper thermal insulation cover is, the stronger an ability of the upper thermal insulation cover to resist a heat transfer is, and the better a thermal insulation effect of the upper thermal insulation cover is.

The deviation value between the thermal resistance values of the upper thermal insulation cover comprises a radial deviation value between the thermal resistance values of the upper thermal insulation cover and an axial deviation value between the thermal resistance values of the upper thermal insulation cover. The radial deviation value between the thermal resistance values of the upper thermal insulation cover can be obtained by measuring the thermal resistance values of the upper thermal insulation cover in both sides of a radial direction of the upper thermal insulation cover, and calculating a difference between the thermal resistance values of the upper thermal insulation cover in both sides of the radial direction of the upper thermal insulation cover, that is obtaining the radial deviation value between the thermal resistance values of the upper thermal insulation cover. The axial deviation value between the thermal resistance values of the upper thermal insulation cover can be obtained by measuring the thermal resistance values of the upper thermal insulation cover in both sides of an axial direction of the upper thermal insulation cover, and calculating a difference between the thermal resistance values of the upper thermal insulation cover in both sides of the axial direction of the upper thermal insulation cover, that is obtaining the axial deviation value between the thermal resistance values of the upper thermal insulation cover.

Similarly, adopting a same method, it is able to achieve the thermal resistance value of the lower thermal insulation cover and the deviation value between the thermal resistance values of the lower thermal insulation cover, the deviation value between the thermal resistance values of the lower thermal insulation cover comprises a radial deviation value between the thermal resistance values of the lower thermal insulation cover and an axial deviation value between the thermal resistance values of the lower thermal insulation cover.

The shape factor of the crystal growth channel refers to a size value of the crystal growth channel, in an embodiment, when the crystal growth channel is in a cylinder shape, the shape factor of the crystal growth channel comprises: a diameter and a height of the crystal growth channel; when the crystal growth channel is a cuboid, the shape factor of the crystal growth channel comprises a length, a width and a height of the crystal growth channel; the shape factor of the crystal growth channel will also affect the thermal field distribution of a crystal growth environment, thereby affecting a growth performance of the crystal.

Also, the shape factor of the crystal growth observation hole refers to a size value of the crystal growth observation hole. The shape of the crystal growth observation hole will also affect the thermal field distribution of the crystal growth environment, thereby affecting a growth performance of the crystal.

Since the crucible is heated by the induction coil and the heating ring, the relative height between the crucible and the induction coil, and the relative height between the heating ring and the induction coil, will affect the thermal field distribution of the crystal growth environment.

In the present embodiment, the control data comprises a width of a mold opening gap and a thickness of the mold opening gap, a molten high resistance gallium oxide is mainly transported to the top of the mold through the capillary siphon effect of the mold opening gap, so as to grow into the high resistance gallium oxide crystal gradually on the seed crystal. Therefore, the width and the thickness of the mold opening gap have a greater impact on the quality of the high resistance gallium oxide single crystal.

Following using a device for growing the high resistance gallium oxide crystal, the thermal resistance of the upper insulation cover, the thermal resistance of the lower insulation, the deviation of the thermal resistance of the upper insulation, and the deviation of the thermal resistance of the lower insulation will change, but not in a short time, thus it is possible to recheck the environmental data after a certain number of crystal growths.

The heating power refers to a heating power of the heating ring to the crucible; the cooling power refers to a power of cooling an inner environment of the crystal growth furnace by using a liquid; the atmosphere type refers to a type of a gas introduced into the crystal growth furnace, including $O_2$, Ar, $N_2$, $CO_2$ and more; the cavity pressure refers to a pressure in the crystal growth furnace, the gas flow refers to a flow of a gas flowing into the crystal growth furnace; the seed crystal rod pulling speed refers to a speed at which a seed crystal rod is pulled up during a crystal growth process; a crystal rotation speed refers to a speed at which the seed crystal rod drives the crystal to rotate during the crystal growth process, and the crystallization rate refers to a ratio of a raw material of the molten high resistance gallium oxide forming a crystal; a diameter ratio of the crystal to the crucible refers to a ratio of a diameter of a produced crystal to a diameter of the crucible. These parameters are all the control parameters affecting the preparation of the crystal by the EFG method.

In one implementation method of the present embodiment, the step S210, according to the seed crystal data, the environmental data, and the control data, obtaining the preprocessed preparation data, further comprises:

S211, according to the seed crystal data, the environmental data, and the control data, determining a preparation vector, a first element in the preparation vector is one of the half-height width of the seed crystal diffraction peak, the deviation value of the half-height width of the seed crystal diffraction peak, the seed crystal thickness and the seed crystal width; a second element in the preparation vector is one of the thermal resistance value of the upper thermal insulation cover, the deviation value between the thermal resistance values of the upper thermal insulation cover, the shape factor of the crystal growth channel, the shape factor of the crystal growth observation hole, the thermal resistance value of the lower thermal insulation cover, the deviation value between the thermal resistance values of the lower thermal insulation cover, the relative height between the crucible and the heating coil, the relative height between the heating ring and the heating coil, the width of the mold opening gap, the thickness of the mold opening gap, the doping element concentration, and the doping element type; the doping element type comprises: Fe, Ca, Zn, Co, Ti, Ni, Mg, Al and Cu; a third element in the preparation vector is one of the heating power, the cooling power, the atmosphere type, the cavity pressure, the gas flow, and the seed rod pulling speed.

S212, determining the preprocessed preparation data, according to the preparation vector.

Specifically, determining a preparation vector (A, B, C) according to a seed crystal data A, an environment data B and a control data C. The seed crystal data A is selected from: a half-height width A1 of a seed crystal diffraction peak, a deviation value A2 of the half-height width of the seed crystal diffraction peak, a seed crystal thickness A3 and a seed crystal width A4. The environmental data B is selected from: a thermal resistance value B1 of the upper thermal insulation cover, a deviation value B2 between the thermal resistance values of the upper thermal insulation cover, a shape factor B3 of the crystal growth channel, a shape factor B4 of the crystal growth observation hole, a thermal resistance value B5 of the lower thermal insulation cover, a deviation value B6 between the thermal resistance values of the lower thermal insulation cover, a relative height B7 between the crucible and the heating coil, a relative height B8 between the heating ring and the heating coil, a width B9 of the mold opening gap, a thickness B10 of the mold opening gap, a doping element concentration B11 and a doping element type B12. The control data C is selected from: a heating power C1, a cooling power C2, an atmosphere type C3, a cavity pressure C4, a gas flow C5, and a seed crystal rod pulling speed C6. That is, the A in the preparation vector (A, B, C) may be one of the A1, A2, A3, A4, B may be one of the B1, B2, B3, B4, B5, B6, B7, B8, B9, B10, B11, B12, C may be one of the C1, C2, C3, C4, C5, C6. Thus it is possible to form 288 preparation vectors.

Arranging all of the preparation vectors according to a sequence number to form a matrix, and then obtain the preprocessed preparation data.

Specifically, the preprocessed preparation data is as follows:

Specifically, the predicted quality data comprises: a predicted crack data, a predicted miscellaneous crystal data, a predicted half-height width of the diffraction peak, a predicted deviation value of the half-height width of the diffraction peak, a predicted shoulder symmetry of the high resistance gallium oxide crystal, a predicted left border extending and retracting degree of the high resistance gallium oxide crystal, a predicted right border extending and retracting degree of the high resistance gallium oxide crystal, a predicted thickness of the high resistance gallium oxide crystal, and a predicted deviation value of the thickness of the high resistance gallium oxide crystal, a predicted radius deviation value of the resistivity and a predicted axial deviation value of the resistivity. Among them, the crack data refers to a crack level data, and the predicted crack data refers to a predicted crack level data. In one embodiment, the cracks can be divided into a plurality of levels, for example, if the cracks are divided into 3 levels, the crack data are: 1, 2 and 3 respectively.

A miscellaneous crystal data refers to a miscellaneous crystal level data, and the predicted miscellaneous crystal data refers to a miscellaneous crystal level data obtained by prediction. In an embodiment, the miscellaneous crystal can be divided into a plurality of levels. For example, the miscellaneous crystal is divided into 3 levels, and the miscellaneous crystal data are: 1, 2 and 3, respectively.

The predicted half-height width of the diffraction peak refers to a half-height width of the diffraction peak obtained by prediction; the predicted radial deviation value of the half-height width of the diffraction peak refers to a predicted deviation value of the half-height width of the diffraction peak at a radial direction; the predicted axial deviation value of the half-height width of the diffraction peak refers to a predicted deviation value of the half-height width of the diffraction peak at an axial direction.

In a plurality of embodiments, the trained neural network model is obtained by adopting a plurality of following training steps:

S01, acquiring a training data of preparing the high resistance gallium oxide single crystal by the EFG method and a corresponding actual quality data, among them, the training data comprises: a seed crystal training data, an environmental training data, and a control training data;

Specifically, the training data refers to a data of the high resistance gallium oxide single crystal prepared by the EFG method and used for training, and the actual quality data refers to a data of an actual quality of the high resistance gallium oxide single crystal prepared by the EFG method. By forming a training set through the training data and the actual quality data, and training a preset neural network model according to the training set, the trained neural network model is obtained.

$$\begin{bmatrix} (A1\,B1\,C1) & \cdots & (A1\,B7\,C1)(A2\,B1\,C1) & \cdots & (A2\,B7\,C1)(A3\,B1\,C1) & \cdots & (A3\,B12\,C1) \\ \vdots & \ddots & \cdot & \cdot & \ddots & \cdot & \cdot & \ddots & \cdot \\ (A1\,B1\,C9) & \cdots & (A1\,B7\,C9)(A2\,B1\,C9) & \cdots & (A2\,B7\,C9)(A3\,B1\,C9) & \cdots & (A3\,B12\,C9) \end{bmatrix}$$

Of course, it is possible to adopt other arrangement to obtain the preprocessed preparation data.

S300, inputting the preprocessed preparation data into a trained neural network model, acquiring a predicted quality data corresponding to the high resistance gallium oxide single crystal through the trained neural network model.

When collecting the data to obtain the training set, the high resistance gallium oxide single crystal is prepared by the EFG method, and the data for preparing the high resistance gallium oxide single crystal is recorded as the training data. After obtaining the high resistance gallium oxide single crystal, a quality thereof is analyzed to obtain the actual quality data. In order to facilitate the training of the neural network model, it may collect as much data as possible to form the training set.

S02, preprocessing the training data to obtain a preprocessed training data.

Specifically, after obtaining the training data, the training data is preprocessed to obtain the preprocessed training data. A preprocess process may refer to the step S200.

S03, inputting the preprocessed training data into a preset neural network model, and obtaining a predicted training generated quality data corresponding to the preprocessed training data through the preset neural network model;

Specifically, inputting the preprocessed training data into a preset neural network model, and obtaining the predicted training generated quality data through the preset neural network model. The predicted training generated quality data comprises: a predicted training generated crack data, a predicted training generated miscellaneous crystal data, a predicted training generated half-height width of the diffraction peak, a predicted training generated radial deviation value of the half-height width of the diffraction peak, and a predicted training generated axial deviation value of the half-height width of the diffraction peak.

S04, adjusting and correcting a plurality of model parameters of the preset neural network model to obtain a trained neural network model, according to the predicted training generated quality data and the actual quality data.

Specifically, correcting the model parameters of the preset neural network model according to the predicted training generated quality data and the actual quality data, and continuing to run the steps of inputting the preprocessed training data into the preset neural network model, and obtaining the predicted training generated quality data corresponding to the preprocessed training data through the preset neural network model (that is, the step S03), until the preset training conditions are met, thus obtaining the trained neural network model.

Specifically, correcting the model parameters of the preset neural network model according to the predicted training generated quality data and the actual quality data, and continuing to run the steps of inputting the preprocessed training data into the preset neural network model, and obtaining the predicted training generated quality data corresponding to the preprocessed training data through the preset neural network model, until the preset training conditions are met, thus obtaining the trained neural network model, that is, if the preset neural network model meets the preset training conditions, the trained neural network model will be obtained. If the preset neural network model doesn't meet the preset training conditions, go back to the step S03, until the preset neural network model meets the preset training conditions, and the trained neural network model will be obtained.

In one implementation method of an embodiment of the present application, determining a loss function value of the preset neural network model according to the predicted training generated quality data and the actual quality data, and correcting the model parameters of the preset neural network model according to the loss function value. Specifically, adopting a gradient-based method to correct the parameters of the preset neural network model, and after the loss function value of the preset neural network model is determined, correcting a gradient of the parameters of the preset neural network model, the parameters of the preset neural network model, and a preset learning rate, according to the loss function value, and determining a corrected parameter of the preset neural network model.

The preset training conditions comprise: the loss function value meets a preset requirement and/or a preset number of training times of the neural network model reaches a preset number of times.

The preset requirement is determined according to accuracy and efficiency of the preset neural network model, in one embodiment, the loss function value of the preset neural network model reaches a minimum value or has no longer changes. The preset number of times is a preset maximum number of training times of the neural network model, for example, 4000 times.

The loss function of the preset neural network model comprises: a mean square error, a root mean square error, a mean absolute error, and more.

In one implementation method of an embodiment of the present application, the preset neural network model comprises: a feature extraction module and a fully connected module.

In one embodiment, the preset neural network model comprises: a first convolution unit, a second convolution unit, a third convolution unit, a fourth convolution unit, and a fully connected unit. Specifically, the first convolution unit comprises: two convolution layers and one pooling layer. Each of the second convolution unit, the third convolution unit, and the fourth convolution unit comprises three convolution layers and one pooling layer. The fully connected unit comprises three fully connected layers.

The convolution layers and the fully connected layers are responsible for mapping and transforming an input data. The process will use a plurality of parameters including a weight and a bias, and also use an activation function. The pooling layer is a fixed function operation. Specifically, the convolution layer plays a role in extracting the features; the pooling layer performs a pooling operation on an input feature to change a spatial size thereof; and the fully connected layer connects all data in a previous layer.

In a plurality of implementation methods, the step S03, inputting the preprocessed training data into a preset neural network model, and obtaining a predicted training generated quality data corresponding to the preprocessed training data through the preset neural network model, comprises:

S031, inputting the preprocessed training data into the feature extraction module, and obtaining a feature vector corresponding to the preprocessed training data through the feature extraction module;

S032, inputting the feature vector into the fully connected module, and obtaining the predicted training generated quality data corresponding to the preprocessed training data through the fully connected module.

Specifically, inputting the preprocessed training data into the preset neural network model, outputting the feature vector corresponding to the preprocessed training data through the feature extraction module in the preset neural network model, then inputting the feature vector into the fully connected module, and obtaining the predicted training generated quality data corresponding to the preprocessed training data output by the fully connected module.

Figure 3:
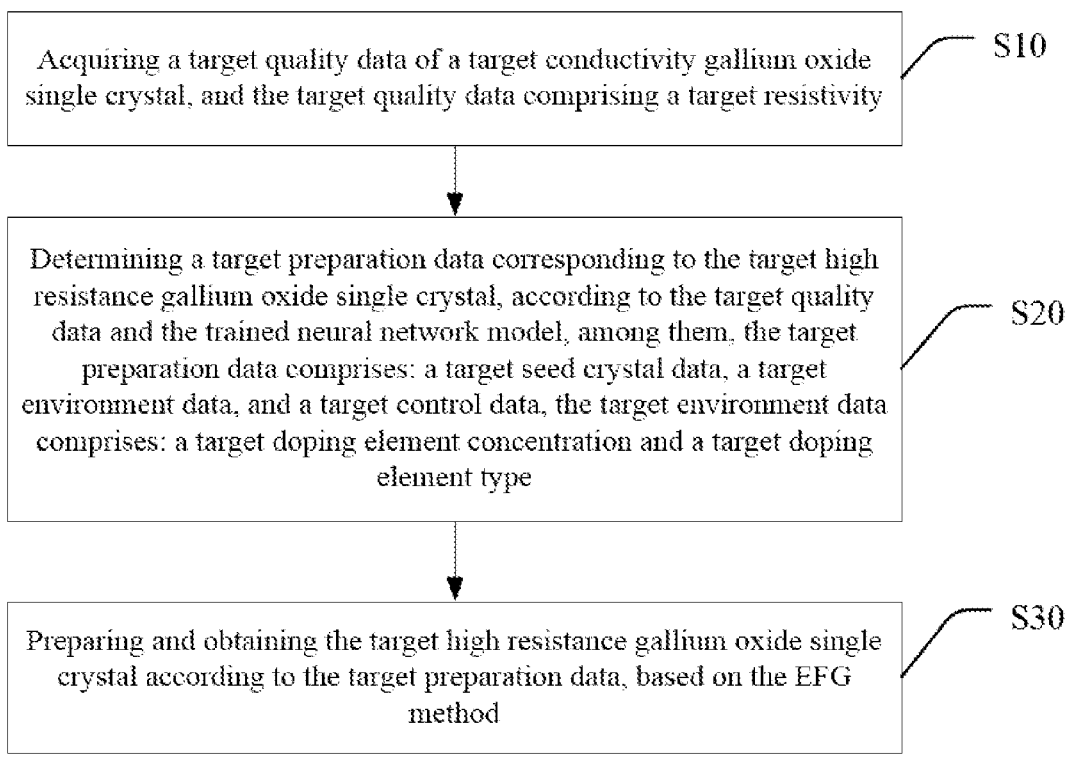
FIG. 3 illustrates a flowchart on a preferred embodiment of the preparation method of the high resistance gallium oxide based on deep learning and the EFG method provided by the present application.

According to the quality prediction method of the high resistance gallium oxide based on deep learning and the EFG method, the present embodiment provides a preparation method of the high resistance gallium oxide based on deep learning and the EFG method, shown as FIG. 3, the preparation method comprises:

S10, acquiring a target quality data of a target conductivity gallium oxide single crystal, and the target quality data comprising a target resistivity.

Specifically, if a target high resistance gallium oxide single crystal shall be obtained, it is possible to determine a target quality data of the target high resistance gallium oxide single crystal first, that is, determining the quality data of a desired high resistance gallium oxide single crystal. The target quality data further comprises: a target crack data, a target miscellaneous crystal data, a target half-height width of the diffraction peak, a deviation value of the target half-height width of the diffraction peak, a shoulder symmetry of the target high resistance gallium oxide crystal, a left border extending and retracting degree of the target high resistance gallium oxide crystal, a right border extending and retracting degree of the target high resistance gallium oxide crystal, a thickness of the target high resistance gallium oxide crystal, a deviation of the thickness of the target high resistance gallium oxide crystal, a radial deviation value of the target resistivity, and an axial deviation value of the target resistivity.

S20, determining a target preparation data corresponding to the target high resistance gallium oxide single crystal, according to the target quality data and the trained neural network model, among them, the target preparation data comprises: a target seed crystal data, a target environment data, and a target control data, the target environment data comprises: a target doping element concentration and a target doping element type.

Specifically, determining the target preparation data corresponding to the target high resistance gallium oxide single crystal, according to the target quality data and the trained neural network model. It should be noted that, since different preparation data may obtain a same quality data, when determining the target preparation data corresponding to the target conductivity type gallium oxide single crystal according to the target quality data and the trained neural network model, the target preparation data is not unique, and a target preparation data is determined according to a control difficulty of each of the plurality of target preparation data, so as to facilitate obtaining the target high resistance gallium oxide single crystal.

In a plurality of implementation methods, the step S20, determining the target preparation data corresponding to the target high resistance gallium oxide single crystal, according to the target quality data and the trained neural network model, comprises:

S21, acquiring a preset preparation data, preprocessing the preset preparation data, and obtaining a preprocessed preset preparation data;

S22, inputting the preprocessed preset preparation data into the trained neural network model, and obtaining a predicted quality data corresponding to the preprocessed preset preparation data through the trained neural network model;

S23, correcting the preset preparation data and obtaining the target preparation data corresponding to the target high resistance gallium oxide single crystal according to the predicted quality data and the target quality data.

Specifically, it is possible to preset a preparation data, and preprocess the preset preparation data, to obtain the preprocessed preset preparation data, a specific preprocessing process may refer to the step S200. Inputting the preprocessed preset preparation data into the trained neural network model, it is possible to obtain a predicted quality data correcting the preprocessed preset preparation data, then correcting the preset preparation data according to the predicted quality data and the target quality data, when a difference between the predicted quality data and the target quality data is less than a preset threshold, the preset preparation data after correction is possible to be the target preparation data.

S30, preparing and obtaining the target high resistance gallium oxide single crystal according to the target preparation data, based on the EFG method.

Specifically, after obtaining the target preparation data, it is possible to preparing and obtaining the target high resistance gallium oxide single crystal according to the target preparation data, based on the EFG method.

Figure 4:
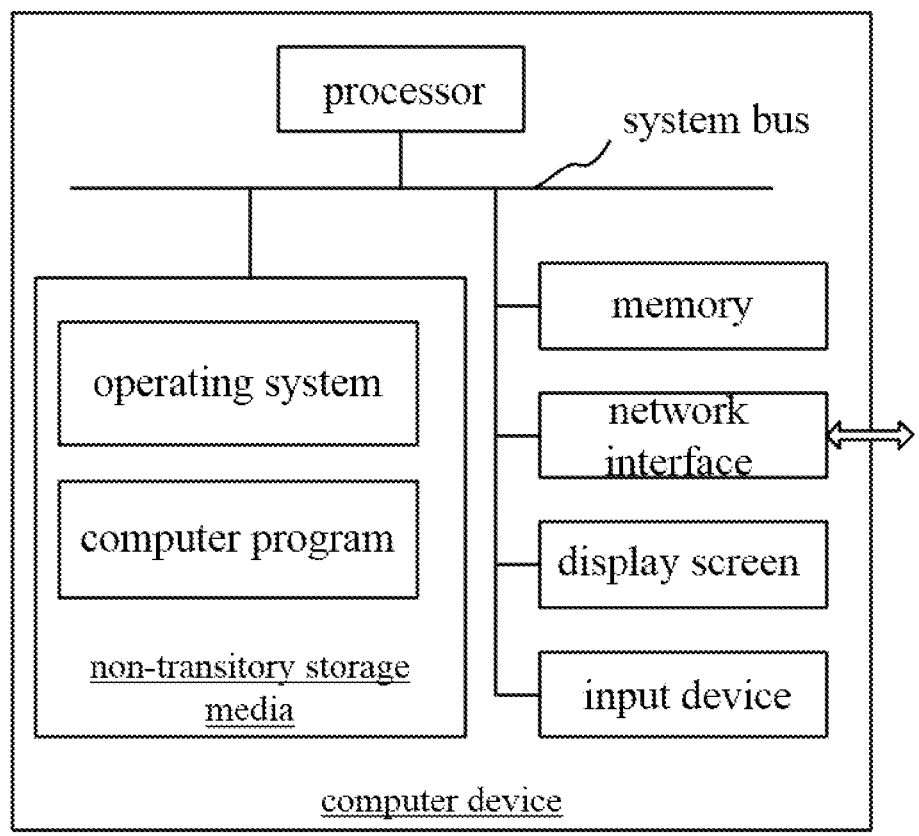
FIG. 4 illustrates an internal structure diagram of a preparation system of the high resistance gallium oxide based on deep learning and the EFG method provided by the present application.

Based on the prediction method or the preparation method, the present application provides a preparation system of the high resistance gallium oxide based on deep learning and the EFG method, the preparation system may be a computer device, an inner structure thereof is shown as FIG. 4. The preparation system comprises a processor, a storage, a network interface, a display screen and an input device connected by a system bus. Among them, the processor thereof is applied to providing a calculation and control ability. The storage thereof comprises a non-transitory storage media and an internal memory. The non-transitory storage media has an operating system and a computer program stored. The internal memory provides an environment for running the operating system and the computer program in the non-transitory storage media. The network interface thereof is applied to communicating with a plurality of external terminals through a network connection. The computer program is executed by the processor to realize the prediction method of the high resistance gallium oxide based on deep learning and the EFG method or the preparation method of the high resistance gallium oxide based on deep learning and the EFG method. The display screen of the system may be a liquid crystal display screen or an electronic ink display screen, and the input device thereof may be a touch layer covered on the display screen, or a button, a trackball or a touchpad arranged on a shell of the preparation system, further may be an external keyboard, a touchpad or a mouse, and more.

Those skilled in the art may understand that, FIG. 4 shows only a block diagram of part structures related to a solution of the present application, instead of constituting a limitation on a system to which the solution of the present application is applied. A specific system may comprise more or less parts than those shown in the figure, may have some parts combined, or have a different arrangement of parts.

In one embodiment, a preparation system of the high resistance gallium oxide based on deep learning and the EFG method is provided, comprising a storage and a processor, the storage stores a computer program. When the processor executes the computer program, the steps of the quality prediction method or the steps of the preparation method are implemented.

It should be understood that, the application of the present application is not limited to the above examples listed. Ordinary technical personnel in this field can improve or change the applications according to the above descriptions, all of these improvements and transforms should belong to the scope of protection in the appended claims of the present application.

What is claimed is:

1. A quality prediction and preparation method of high resistance gallium oxide based on a deep learning and an edge-defined film-fed growth (EFG) method, comprising:
preparing a seed crystal in a crucible by the EFG method, wherein the seed crystal and a melt body are fully welded and connected prior to seeding and necking;

determining a preparation data of preparing a high resistance gallium oxide single crystal by the EFG method, the preparation data comprising seed crystal data measured from the seed crystal, an environment data and a control data, the control data comprising a doping element concentration and a doping element type; and preprocessing the preparation data to obtain a preprocessed preparation data and a training data;

training the neural network model using the training data;

inputting the preprocessed preparation data into the trained neural network model, determining, by the trained neural network model, targeted quality data corresponding to the high resistance gallium oxide single crystal through the trained neural network model, the targeted quality data comprising a predicted resistivity; and preparing a targeted high resistance gallium oxide crystal according to the targeted quality data.

2. The quality prediction and preparation method of the high resistance gallium oxide based on deep learning and the EFG method according to claim 1, wherein the preprocessing of the preparation data to obtain the preprocessed preparation data, comprises:

according to the seed crystal data, the environmental data, and the control data, obtaining the preprocessed preparation data, and the preprocessed preparation data is a matrix formed by the seed crystal data, the environmental data, and the control data.

3. The quality prediction and preparation method of the high resistance gallium oxide based on deep learning and the EFG method according to claim 2, wherein the seed crystal data comprises: a half-height width of a seed crystal diffraction peak, a deviation value of the half-height width of the seed crystal diffraction peak, a seed crystal thickness and a seed crystal width;

the environmental data further comprising: a thermal resistance value of an upper thermal insulation cover, a deviation value between the thermal resistance values of the upper thermal insulation cover, a shape factor of a crystal growth channel, a shape factor of a crystal growth observation hole, a thermal resistance value of a lower thermal insulation cover, a deviation value between the thermal resistance values of the lower thermal insulation cover, a relative height between a crucible and a heating coil, a relative height between a heating ring and the heating coil, a width of a mold opening gap, and a thickness of the mold opening gap; and the control data comprising: a heating power, a cooling power, an atmosphere type, a cavity pressure, a gas flow, and a seed crystal rod pulling speed.

4. The quality prediction and preparation method of the high resistance gallium oxide based on deep learning and the EFG method according to claim 3, wherein obtaining the preprocessed preparation data comprises:

according to the seed crystal data, the environmental data, and the control data, determining a preparation vector; wherein a first element in the preparation vector is one of the half-height width of the seed crystal diffraction peak, the deviation value of the half-height width of the seed crystal diffraction peak, the seed crystal thickness and the seed crystal width; a second element in the preparation vector is one of the thermal resistance value of the upper thermal insulation cover, the deviation value between the thermal resistance values of the upper thermal insulation cover, the shape factor of the crystal growth channel, the shape factor of the crystal growth observation hole, the thermal resistance value of the lower thermal insulation cover, the deviation value between the thermal resistance values of the lower thermal insulation cover, the relative height between the crucible and the heating coil, the relative height between the heating ring and the heating coil, the width of the mold opening gap, the thickness of the mold opening gap, the doping element concentration, and the doping element type, the type of the doping element comprising: Si, Ge, Sn, Zr, Hf, In, Ta, Nb, V, W, and Mo; a third element in the preparation vector is one of the heating power, the cooling power, the atmosphere type, the cavity pressure, the gas flow, and the seed rod pulling speed; and determining the preprocessed preparation data, according to the preparation vector.

5. The quality prediction and preparation method of the high resistance gallium oxide based on deep learning and the EFG method according to claim 1, wherein the predicted quality data comprises: a predicted crack data, a predicted miscellaneous crystal data, a predicted half-height width of the diffraction peak, a predicted deviation of the half-height width of the diffraction peak, a predicted shoulder symmetry of the high resistance gallium oxide crystal, a predicted left border extending and retracting degree of the high resistance gallium oxide crystal, a predicted right border extending and retracting degree of the high resistance gallium oxide crystal, a predicted thickness of the high resistance gallium oxide crystal, a deviation of the predicted thickness of the high resistance gallium oxide crystal, a predicted radial deviation of the resistivity, and a predicted axial deviation of the resistivity.

6. The quality prediction and preparation method of the high resistance gallium oxide based on deep learning and the EFG method according to claim 1, wherein the trained neural network model is trained and obtained by:

acquiring a training data of preparing the high resistance gallium oxide single crystal by the EFG method and a corresponding actual quality data, wherein the training data comprises: a seed crystal training data, an environmental training data, and a control training data;

preprocessing the training data to obtain a preprocessed training data;

inputting the preprocessed training data into a preset neural network model, and obtaining a predicted training generated quality data corresponding to the preprocessed training data through the preset neural network model; and adjusting and correcting a plurality of model parameters of the preset neural network model to obtain a trained neural network model, according to the predicted training generated quality data and the actual quality data.

7. The quality prediction and preparation method of the high resistance gallium oxide based on deep learning and the EFG method according to claim 6, wherein the preset neural network model comprises: a feature extraction module and a fully connected module, the step of inputting the preprocessed training data into the preset neural network model, and obtaining the predicted training generated quality data corresponding to the preprocessed training data through the preset neural network model, comprises:

inputting the preprocessed training data into the feature extraction module, and obtaining a feature vector corresponding to the preprocessed training data through the feature extraction module; and inputting the feature vector into the fully connected module, and obtaining the predicted training generated quality data corresponding to the preprocessed training data through the fully connected module.

8. A preparation method of the high resistance gallium oxide based on deep learning and the EFG method, wherein the preparation method, comprising:
preparing a seed crystal in a crucible by the EFG method, wherein the seed crystal and a melt body are fully welded and connected prior to seeding and necking;
determining target quality data of a target conductivity gallium oxide single crystal, the target quality data comprising a target resistivity;
determining target preparation data corresponding to the target high resistance gallium oxide single crystal, according to the target quality data and a trained neural network model, the target preparation data comprising: a target seed crystal data measured from the prepared seed crystal, a target environment data, and a target control data, the target environment data comprising a target doping element concentration and a target doping element type, wherein the trained neural network model is trained with a training set;
determining, by the trained neural network model, targeted property data corresponding to the high resistance gallium oxide single crystal, the targeted quality data comprising a predicated resistivity; and
preparing and obtaining the target high resistance gallium oxide single crystal according to the target preparation data.

9. The preparation method of the high resistance gallium oxide based on deep learning and the EFG method according to claim 8, wherein determining the target preparation data corresponding to the target high resistance gallium oxide single crystal, according to the target quality data and the trained neural network model, comprises:
acquiring a preset preparation data, preprocessing the preset preparation data, and obtaining a preprocessed preset preparation data;
inputting the preprocessed preset preparation data into the trained neural network model, and obtaining a predicted quality data corresponding to the preprocessed preset preparation data through the trained neural network model; and
correcting the preset preparation data and obtaining the target preparation data corresponding to the target high resistance gallium oxide single crystal according to the predicted quality data and the target quality data.

10. A preparation system of the high resistance gallium oxide based on deep learning and the EFG method, comprising a non-transitory memory and a processor, a computer program is stored in the non-transitory memory, the processor executes the computer program to operate the steps of the quality prediction method according to claim 1.

* * * * *